United States Patent [19]
Goldenberg

[11] Patent Number: 5,843,001
[45] Date of Patent: Dec. 1, 1998

[54] CONNECTOR FOR A REPLACEABLE BIOPSY NEEDLE

[76] Inventor: Alec Goldenberg, 4 Washington Sq. Village #8P, New York, N.Y. 10012

[21] Appl. No.: 932,109

[22] Filed: Sep. 17, 1997

[51] Int. Cl.[6] ........................................................ A61B 5/10
[52] U.S. Cl. ............................ 600/567; 604/283; 403/292
[58] Field of Search ..................................... 600/564–567; 604/165, 283; 403/292, DIG. 4

[56] References Cited

U.S. PATENT DOCUMENTS

| | | | |
|---|---|---|---|
| Re. 34,466 | 12/1993 | Taylor et al. ............................ | 600/585 |
| 2,473,388 | 6/1949 | Rambo ..................................... | 403/292 |
| 4,258,722 | 3/1981 | Sessions et al. . | |
| 4,262,676 | 4/1981 | Jamshidi . | |
| 4,266,555 | 5/1981 | Jamshidi . | |
| 4,356,828 | 11/1982 | Jamshidi . | |
| 4,461,305 | 7/1984 | Cibley . | |
| 4,752,292 | 6/1988 | Lopez et al. ............................ | 604/283 |
| 4,785,826 | 11/1988 | Ward . | |
| 5,005,585 | 4/1991 | Mazza . | |
| 5,429,138 | 7/1995 | Jamshidi . | |
| 5,522,398 | 6/1996 | Goldenberg et al. . | |
| 5,634,473 | 6/1997 | Goldenberg et al. . | |

*Primary Examiner*—Max Hindenburg
*Attorney, Agent, or Firm*—Darby & Darby

[57] ABSTRACT

A connector assembly is disclosed for connecting the proximal end of a medical device to a handle without compromising the sterility of the working (distal) end of the medical device. The connector assembly comprises a body that is rigidly attached to the proximal end of the medical device. A lever is attached to body and is resiliently biased towards a first position which engages the handle. A lock-tab projects from the lever in a direction generally away from the body and is shaped to be received in a lock-slot within the handle. The lock-tab and handle preferably are shaped to permit a snap-lock engagement of the handle and the body upon insertion of the body within the handle. This assembly can be used on a variety of medical devices and with a variety of handles. One industrial application is a biopsy needle having the connector assembly attached at its proximal end for a secure, snap-lock engagement to the handle.

20 Claims, 4 Drawing Sheets

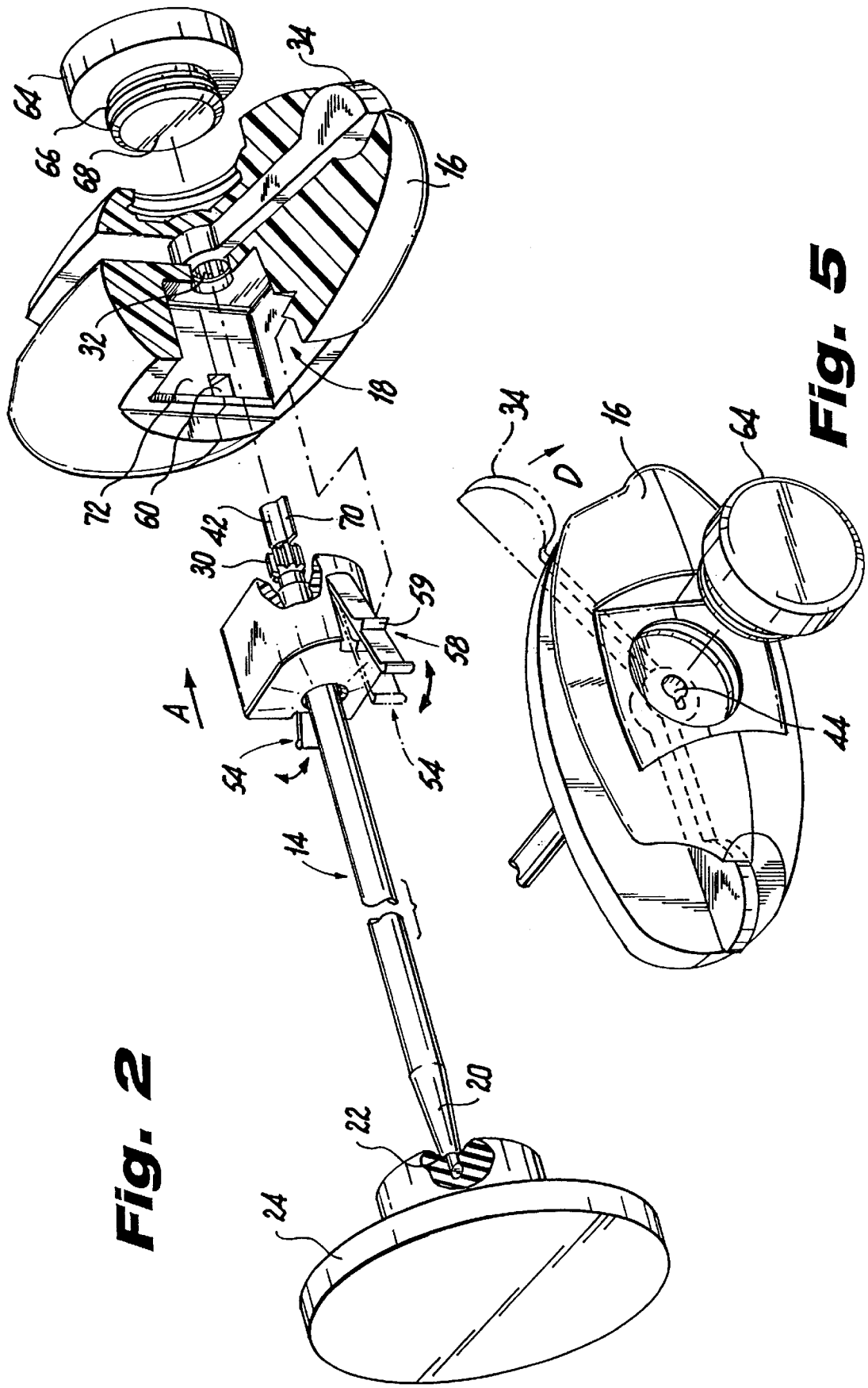

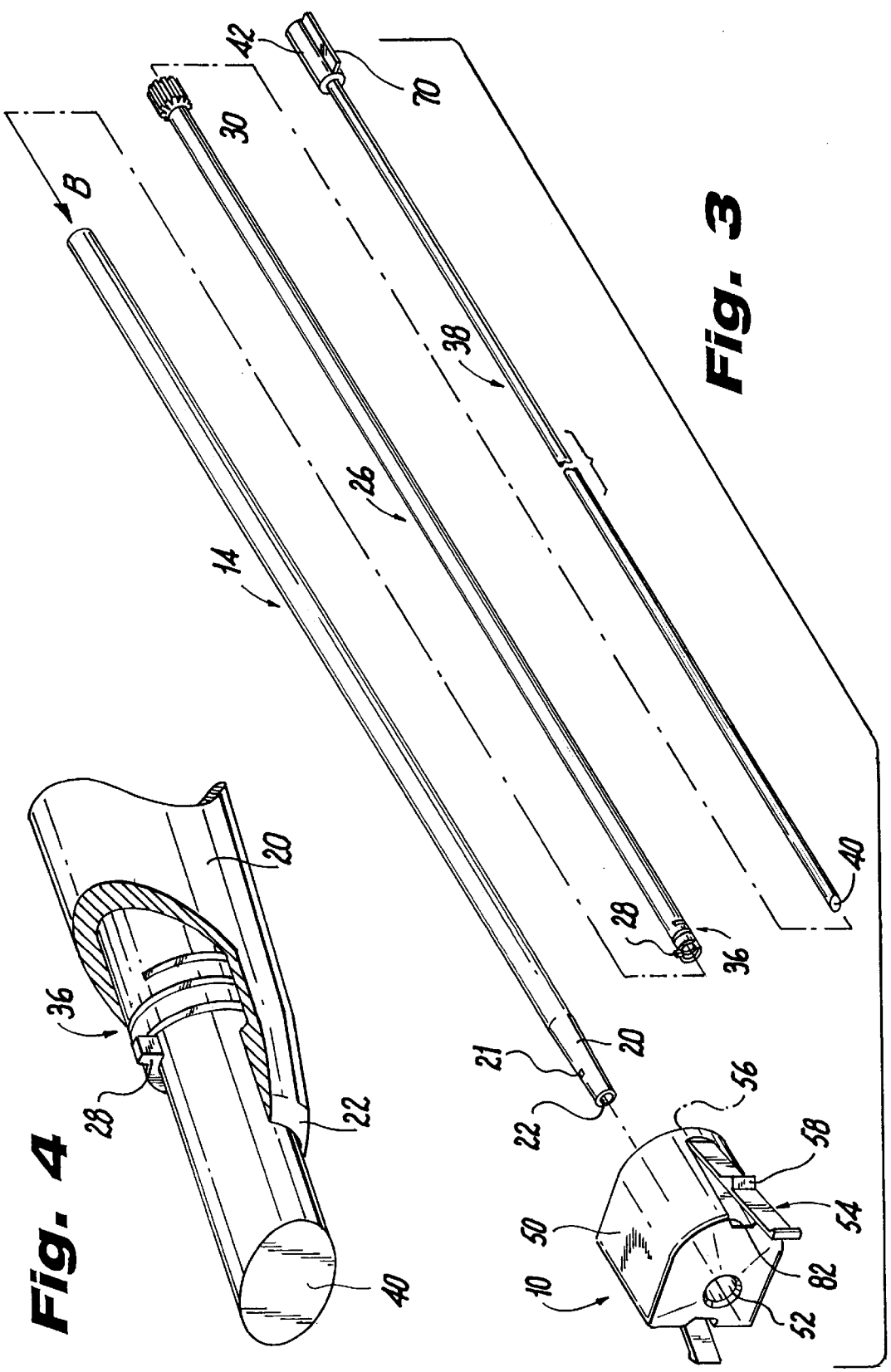

CONNECTOR FOR A REPLACEABLE BIOPSY NEEDLE

FIELD OF THE INVENTION

The present invention relates to an assembly for the proximal end of a medical device, and, more particularly, a needle assembly that is operable when connected to a handle.

BACKGROUND OF THE INVENTION

It is known in the art of medical devices that at least a portion of the device must be sterilized prior to being inserted into a patient. To facilitate the sterilization, the components of the medical device are sometimes sterilized prior to assembly. For example, U.S. Pat. No. 5,429,138 to Jamshidi discloses a biopsy needle that is attachable to a handle by a threaded connector. The common practice is to sterilize both the needle and the handle, either as a complete unit or separately for later assembly by the operator or her assistant.

U.S. Pat. Nos. 5,522,398 and 5,634,473 of Goldenberg et al. also discloses a biopsy needle that threadedly connects to a handle mechanism. The handle mechanism remains external to the patient and does not require sterilization.

A common problem of each of the foregoing biopsy needle designs is that the connection of the needle to the handle requires that a threaded element be passed over the distal tip of the needle to secure the needle to the handle. This threaded connector must also be sterilized or else the sterility of the needle and the safety of the patient will be compromised. Further, the ordinary course of using a biopsy needle requires the operator to twist the needle within the patient and such manipulation could result in a loosening of the threaded connection between the needle and the handle.

The present invention resolves these and other problems by providing a snap lock connection between the operative handle and the medical device.

SUMMARY OF THE INVENTION

In accordance with one aspect of the invention, a connector assembly for snap-connecting the proximal end of a medical device to a handle is disclosed. The assembly comprises a body that is rigidly attached to the proximal end of the medical device. A lever is attached to body and is resiliently biased towards a first position which engages the handle. A lock-tab projects from the lever in a direction generally away from the body and is shaped to be received in a lock-slot within the handle. Preferably, the lock-tab and handle are shaped to permit a snap-lock engagement of the handle and the body upon insertion of the body into the handle. This assembly can be used on a variety of medical devices and with a variety of handles.

In accordance with another aspect of the present invention, a needle assembly is disclosed which includes a hollow needle having a proximal end attached to the above described connector assembly for snap-lock engagement of the needle to the handle. A particular advantage of this construction is that the body at the proximal end of the needle can be securely engaged to a handle without the need for a threaded connector as in the above-described prior art designs. Further, the needle assembly can be provided in a sterile package and assembled to a handle without compromising the sterility of the working end of the needle prior to use.

According to a further aspect of the present invention, a biopsy needle kit is disclosed which includes a hollow needle having the above described connector assembly attached at a proximal end thereof and a handle having an aperture sized to receive the body at the proximal end of the needle. Further, the handle has lock slots positioned within the aperture to receive the lock tabs of the connector assembly. Upon insertion of the needle into the handle, the lever of the body is cammed toward the body until the lock tab of the body aligns with the lock slot of the handle at which moment the lever resiliently moves towards its rest position to lock the needle assembly to the handle. The operator can then use the needle to, for example, extract a biopsy sample, without concern for the sterility of the needle assembly as a result of the steps taken to connect the needle assembly to the handle.

In general terms, the invention provides a connector arrangement which securely engages two elements to one another without the need for manipulating the elements relative to one another (e.g., threading), yet with minimal risk of element separation. More particularly, through the use of camming surfaces, a secure engagement of the elements is automatically achieved by the inventive connector upon insertion of the connector, attached to a first element, into a second element.

These and other objects of the present invention will be appreciated from the following detailed description in conjunction with the detailed accompanying drawings.

BRIEF DESCRIPTION OF THE DRAWINGS

FIG. 2 is a plan view, partially in section, showing the connector assembly of the preferred embodiment in spaced relation to the handle having an aperture sized to receive the assembly;

FIG. 3 is an exploded, perspective view of the biopsy needle of the preferred embodiment;

FIG. 4 is a detailed view, partially in section, of a distal tip of the biopsy needle of FIG. 3;

FIG. 5 is a top perspective view of the handle that may be used with the preferred embodiment of the present invention;

DETAILED DESCRIPTION OF THE INVENTION

Figure 1:
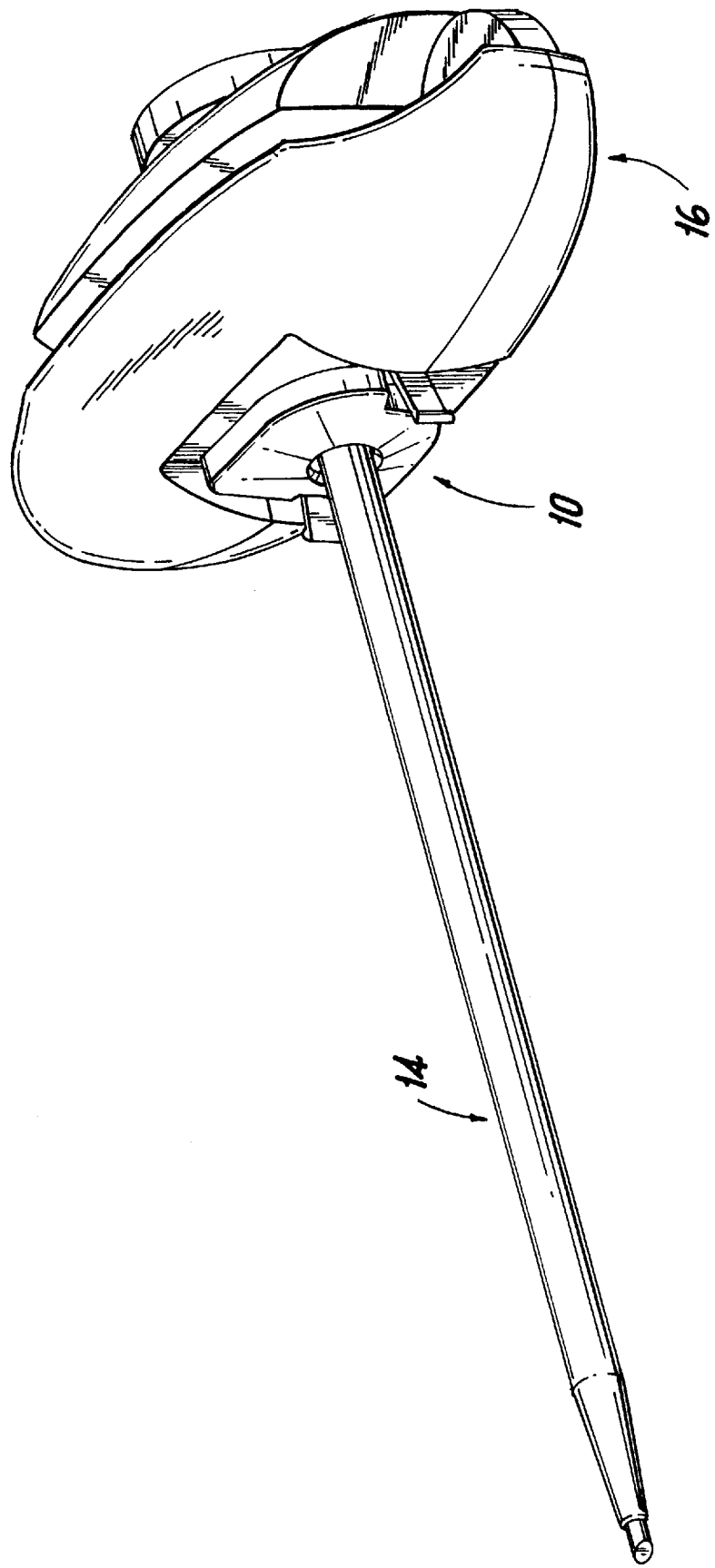
FIG. 1 is a plan view showing the connector assembly of the present invention attached to a biopsy needle and a handle in accordance with a preferred embodiment.

By way of overview in introduction, a preferred embodiment of the invention is illustrated in FIG. 1. The preferred industrial application of the invention is a biopsy needle 14 and operative handle 16 assembly, where the needle 14 and handle 16 are securely engaged to one another by way of a snap-lock connector 10 constructed in accordance with the present invention. The snap-lock connector 10 is fixed to the proximal end of the needle 14 and is shaped to be received in an aperture 18 of the handle 16 (see FIG. 2).

With reference now to FIG. 2, the connector assembly 10 is shown in spaced relation to the handle 16 for insertion into the aperture 18 by moving the connector assembly 10 in the direction of arrow A. The connector assembly 10 has use with many different types of medical devices including catheters and scopes which may be introduced cutaneously or percutaneously into a vessel or other body passageway. The presently preferred embodiment is in the context of biopsy needle design, and the present invention will be described in detail with regard to this presently preferred embodiment and the problems solved in the art of biopsy needle designs, with the understanding that the structure of the connector assembly 10 can be used without limitation with other medical devices.

The biopsy needle 14 has a distally tapering region 20 that is introduced into the body of the patient. The distal tip 22 of the biopsy needle is sharp and preferably is stored within a base 24 or other device until the needle is ready for use.

FIG. 3 illustrates further aspects of the biopsy needle 14. A tube 26 is housed within the needle 14 and advanced in the direction of arrow B into the needle 14 until a tab 28 on the end of the distal end of the tube 26 is received within an aperture 21 in the tapering region 20 of the needle 14 (see FIG. 4). The proximal end of tube 26 includes a knurled surface 30 which is engaged by a toothed aperture 32 of a lever 34 within the handle 16. As described more fully in the aforesaid Goldenberg et al. U.S. Pat. No. 5,522,398 patent, the lever 34 causes rotational movement of the inner tube 26 relative to the outer needle 14 which, in the illustrated embodiment, causes a snare 36 to grab a biopsy sample with a force sufficient to remove the sample from the patient. (Alternatively and equivalently, the tab can be provided on a cylinder (see element 80 in FIG. 8 of the aforementioned Goldenberg et al. U.S. Pat. No. 5,634,473) attached to the distal end of the snare 36.) The biopsy needle 14 further has a stylet 38 slidingly received within the inner tube 26 and outer tube 14 until the distal end 40 of the stylet 38 projects from the outer needle 14 (see FIG. 4). As understood by those of skill in the art, the stylet 40 assists in penetrating the patient's skin and accessing the site from which the sample is extracted. In accordance with an aspect of the present invention, the stylet 38 includes a keyed proximal end 42 which is received within the correspondingly shaped aperture 44 of the handle 16 when the needle is assembled to the handle (see FIG. 5). A particular advantage of this arrangement as compared to known designs is that a sterilized stylet can be inserted within a sterilized needle assembly 14, and the needle 14 and stylet 38 can be connected to the handle 16 without the distal end 40 of the stylet 38 having to pass through the non-sterile handle 16.

With further reference to FIG. 3, the connector assembly 10 of the invention includes an axially asymmetric body 50 having an axial aperture 52 therethrough. The biopsy needle 14 is received within the aperture 52 and preferably forms a tight interference fit therewith. The connector assembly 10 and the outer needle 14 also can be fixed together using an epoxy or a heat welding process. The body 50 includes first and second lever arms 54 which are hingedly attached in the vicinity of a proximal face 56 of the asymmetric body 50. The hinge may be formed by a weakened piece of the same material that forms the body 50. Each of the lever arms 54 includes a lock-tab 58 projecting in a direction away from the body 50 for securely, snap-lock engaging the connector assembly 10 within the aperture 18 of the handle 16. Specifically, the aperture 18 has lock-slots 60 which receive the lock-tabs 58 when the connector assembly 10 is inserted into the handle (see FIG. 2).

The levers 54 are resiliently biased into a first position as shown in FIGS. 2 and 3 and are cammed toward the body to the position shown in phantom in FIG. 2 as the connector assembly 10 is inserted into the aperture 18. However, when the lock-tabs 58 are aligned with the lock-slots 60, the levers 54 resiliently move toward their first position and snap-lock engage the needle 14 into engagement with the handle 16. A distally facing surface 59 of the lock-tabs 58 abuts an edge of the lock-slots 60 and prevents the needle 14 from being withdrawn from the handle 16 unless the levers 54 are manually squeezed in the direction of arrows C (see FIG. 6). A camming surface 57 on the leading edge of the lock-tabs 58 (and/or a camming surface within the aperture 18, aligned with the lock-slots 60) enables an automatic and secure engagement of the body 50 to the handle 60 once the surfaces 59 snap into the lock-slots 60, with minimal risk of the needle 14 (or connector assembly 10) separating from the handle 60.

At the same time that the levers 54 are cammed toward the body during insertion of the connector assembly 10 within the aperture 18, the keyed proximal end 42 of the stylet 38 and the knurled proximal end 30 of the inner tube 26 are received into the handle 16. The knurled proximal end 30 is seated within the toothed aperture 32 of the lever 34, and the keyed proximal end 42 of the stylet projects beyond a correspondingly shaped keyed aperture 44 into a well 62 at the proximal end of the handle 16 (see FIGS. 5 and 6). A cap 64 having threadings 66 is received within the well 62 and secured in place. An abutment surface 68 of the cap 64 prevents the proximal most end 70 of the stylet from retracting in the direction of arrow A relative to the handle 16. This enables the operator to cutaneously insert the needle 14 and stylet 38 into the patient without stylet retraction. Once the skin has been punctured, the cap 64 can be unscrewed and the stylet 38 withdrawn from the needle 14 by grasping the keyed proximal end 42 and withdrawing the stylet 38.

It can be appreciated from the foregoing that the needle 14, inner tube 26, and stylet 38 can be provided in a sterile condition and snap-lock engaged to the handle 16 via the connector assembly 10 without any further element contacting these sterilized components. The handle 16 need not be sterile because that element remains outside of the patient. Therefore, operator can manipulate the handle 16 with the one hand and the operator's other hand remains sterile for contacting the patient or perhaps other devices. Of course, the handle 16 can also be sterilized.

Figure 6:
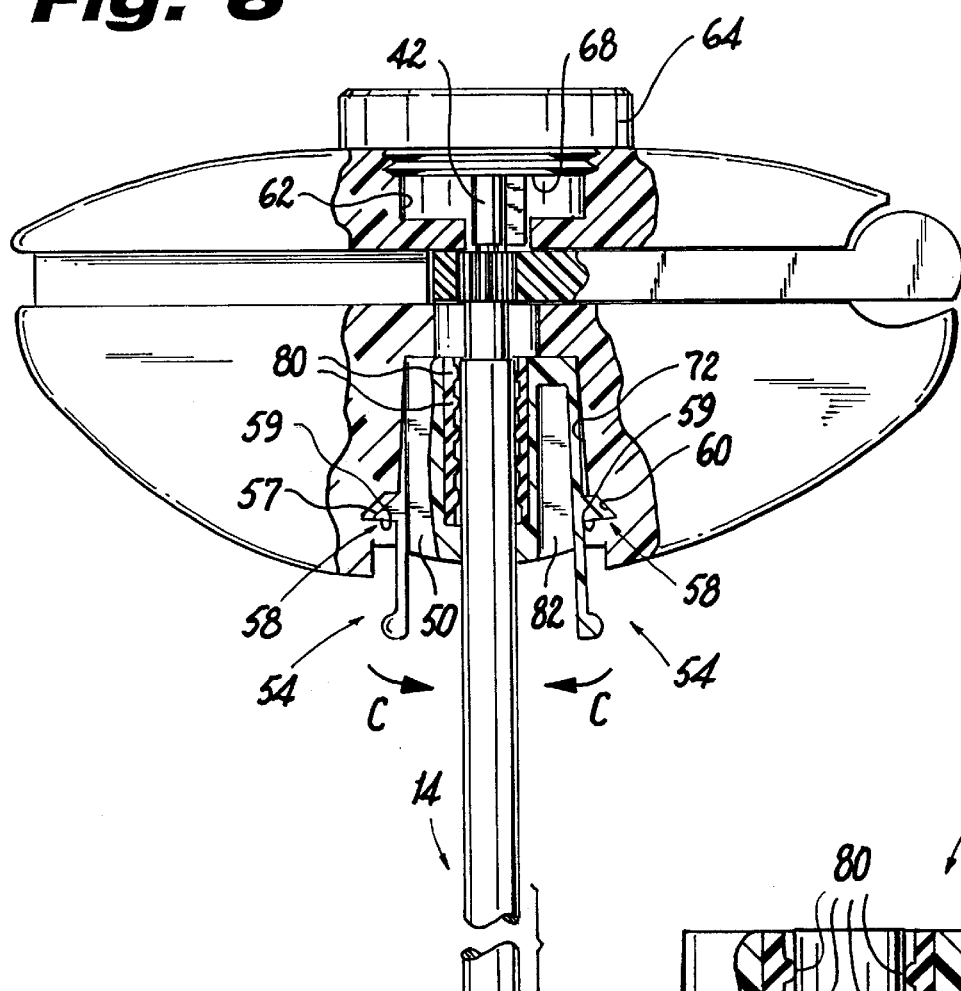
FIG. 6 is a plan view, partially in section, showing the connector assembly fully inserted within the handle of the preferred embodiment.

In FIG. 6, the connector assembly 10 is showing fully inserted within the aperture 18. The lock-tabs 58 of the connector assembly 10 are aligned with and disposed within the lock-slots 60 within the walls 72 of the aperture 18. The lever arm 54 has moved toward its first position but not to its first position, due to an interference between the lever arm 54 and the wall 72. Because the lever arm 54 is not able to fully return to its naturally biased position, the body 50 sits tight within the aperture 18. Also, the axially asymmetric shape of the body 50 minimizes movement of the connector assembly 10 relative to the handle 16 and simplifies insertion (it only fits one way).

FIG. 6 also illustrates slots 82 in the body 50 which facilitate movement of the lever arms 54 toward the body 50 to disengage the lock-tabs 58 from the lock-slots 60, and enable the body 50 to have a relatively low profile shape.

Figure 7:
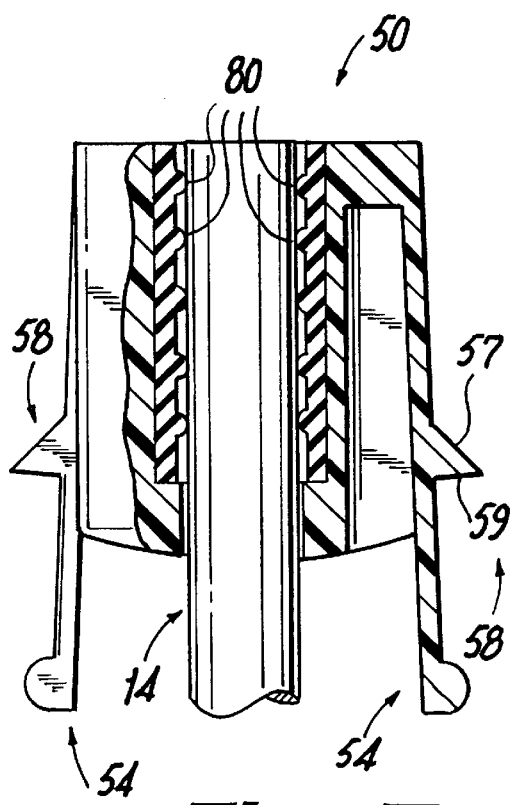
FIG. 7 is a detailed cross-sectional view of a preferred engagement of the connector assembly to a medical device.

The detail view of FIG. 7 is provided to illustrate a series of protuberances 80 within the aperture 52 of the body 50 to fictionally engage the proximal end of the needle 14 or other medical device in accordance with a preferred mode of engaging the connector to the proximal end of the medical device. As noted above, the connector assembly 10 and the needle 14 are afixable using an epoxy or a heat welding process instead of, or in addition to, the aforementioned protuberances 80.

Other designs for the body 50 can be provided within the spirit of the present invention. For example, the lever arms 54 may be arranged in an opposite direction to that shown in the Figures, namely, so as to extend proximal of the proximal face 56 of the asymmetric body 50 with each lever arm 54 hingedly mounted to the body 50 at an acute angle relative to the axis of the body 50. This alternative arrangement still permits the levers 54 to be compressed by the operator so that the lock-tabs 58 can be initially received within the lock-slot 60 and later disengaged. The present design is preferred, however because the body may be provided with an asymmetric shape that fits within a correspondingly shaped aperture 18 of the handle 16. Such an arrangement ensures that the medical device (that is, the needle 14) is snap-locked to the handle with only one orientation. Further, the keyed aperture 44 within the handle 16 ensures that the distal tip 40 of the stylet 38 has a predetermined rotational orientation relative to the distal tip 22 of the needle 14 because the keyed proximal end 42 of the stylet 38 can only be received within the slot 44 with one orientation.

With further reference to FIGS. 5 and 6, the operation of the biopsy needle according to this preferred embodiment is described. With the needle 14 and connector assembly 10 assembled to the handle 16, the knurled end 30 of the inner tube 26 is received within the toothed aperture 32 of the lever 34. Rotation of the lever 34 in the direction of arrow D (FIG. 5) causes rotation of the inner tube 26 relative to the needle 14. In other words, because the needle 14 is rigidly attached to the connector assembly 10 which, in turn, is irrotatably engaged to the handle 16, rotation of the lever 34 causes relative rotation of the inner tube 26. As a result, the snare 36 is wound down to grab a biopsy sample in the manner described in the aforementioned Goldenberg et al. patents.

Of course, the lever can engage the inner tube 26 in other manners to cause a biopsy sample to be grabbed. For example, a lever 34', upon engaging the proximal end 30' of inner tube 26', may cause axial movement of the inner tube 26' relative to the outer needle 14. In such an arrangement, as shown for example in U.S. Pat. No. 4,785,826 to Ward, the inner tube 26' advances towards the distal tip 22 of the needle 14, and a biopsy grasping element 36' at the distal end of the inner tube 26' is cammed inwardly to simultaneously sever or contain a sample and occlude the lumen of the inner tube 26' to prevent the captured sample from escaping. The present invention is not directed to nor limited by a particular arrangement of the distal end 22 of the biopsy needle 14. Rather, the present invention has utility in fields other than biopsy needle design for example in the design of connectors for catheters and other medical devices.

With further reference to FIG. 6, the well 62 under the cap 64 enables the operator to grasp the proximal end 42 of the stylet 38 when the threaded cap 64 is removed.

The connector assembly 10 of the present invention enables a medical device to be snap-locked to another element, for example, a handle or other operating instrument. An advantage of the inventive connector assembly 10 is that it enables the medical device to be maintained in a sterile condition while being assembled to a handle. A further advantage is that it enables a secure connection between the medical device and the handle. A further advantage is that it may be manufactured at a relatively low cost, for example, by injection molding the connector assembly 10 as a unitary element. A particularly preferred material for the connector assembly 10 is plastic and may be made out of any conventional material including LEXAN, PEBAX, nylon, PET or other material.

Preferably, pre-sterilized needles 14 having the connector assembly 10 attached thereto can be sold for use with suitable handle mechanisms 16. Alternatively or in addition, a kit comprising the handle mechanism 16 and one or more needles 14 having a connector assembly 10 attached thereto may be sold together.

The needles 14 may be disposable or reusable after subsequent sterilization. Because the needle is separable from the handle, the conventional sterilization procedure may be simplified by sterilizing the needles only instead of sterilizing both the needle the handle. Such a protocol enables the use of pre-packaged, disposable, sterile needles with a non-sterile handle. Of course, the handle could also be sterilized between uses or on a periodic basis. The benefit that this protocol provides, if the hand used to manipulate the handle does not contact the needle or the patient's skin, is reduced expense in treating patients and elimination of a sterilization step.

The aforementioned Jamshidi, Goldenberg et al. and Ward patents are hereby incorporated by reference as if set forth in their entireties herein. Each of the devices disclosed in the said aforementioned patents, as well as a panoply of other medical devices to numerous to mention, can be modified to include the connector of the present invention to interconnect two elements, including the interconnection of a sterile element to a non-sterile element without compromising the sterility of the working end of the sterile element.

From the foregoing description, it will be clear that the present invention may be embodied in other specific forms without departing from the spirit or essential characteristics thereof. The presently disclosed embodiment is therefore to be considered in all respects as illustrative and not restrictive, the scope of the invention being indicated by the appended claims, and not limited to the foregoing description.

We claim:

1. An assembly for connecting the proximal end of a medical device to a handle, comprising:

a body rigidly attached to the proximal end of the medical device;

a lever attached to the body and resiliently biased towards a first position; and a lock-tab projecting from the lever away from the body.

2. The assembly as in claim 1, wherein the body has an axis and wherein the body has an aperture in the direction of the axis which is sized to receive the proximal end of the medical device.

3. The assembly as in claim 2, wherein the aperture has a plurality of protuberances that frictionally engage the proximal end of the medical device.

4. The assembly as in claim 1, wherein the body, lever, and tab are integral and wherein the lever is attached to the body by a living hinge.

5. The assembly as in claim 1, wherein the body has an axis and is asymmetrically shaped relative to the axis.

6. A needle assembly operable when connected to a handle mechanism, comprising:

a hollow needle having a distal tip and a proximal end;

a body rigidly attached to the proximal end of the needle;

a lever attached to the body and resiliently biased towards a first position; and a lock-tab projecting from the lever away from the body.

7. The assembly as in claim 6, wherein the body has an axis and wherein the body has an aperture in the direction of the axis which is sized to receive the proximal end of the needle.

8. The assembly as in claim 7, wherein the aperture has a plurality of protuberances that frictionally engage the proximal end of the needle.

9. The assembly as in claim 6, wherein the body, lever, and tab are integral and wherein the lever is attached to the body by a living hinge.

10. The assembly as in claim 6, wherein the body has an axis and is asymmetrically shaped relative to the axis.

11. The needle as in claim 6, further comprising a tube movably disposed within the needle, the tube having a proximal end shaped to be operably engaged by the handle mechanism upon insertion of the body into the handle mechanism.

12. The needle as in claim 6, further comprising a stylet axially movably disposed within the hollow needle.

13. The needle as in claim 12, wherein the stylet has a key-shaped proximal end which is irrotatably engaged to the handle mechanism upon insertion of the body into the handle mechanism.

14. A biopsy needle kit, comprising:
   a hollow needle having a distal tip and a proximal end;
   a body rigidly attached to the proximal end of the needle;
   a lever attached to the body and resiliently biased towards a first position;
   a lock-tab projecting from the lever away from the body; and
   a handle having an aperture sized to receive the body at the proximal end of the needle and having a lock-slot positioned within the aperture to receive the lock-tab; the lever camming toward the body during insertion of the body into the aperture and resiliently moving towards the first position when the lock-tab is received in the lock-slot.

15. The assembly as in claim 14, wherein the body has an axis and an aperture in the direction of the axis which is sized to receive the proximal end of the needle.

16. The assembly as in claim 15, wherein the aperture has a plurality of protuberances that frictionally engage the proximal end of the needle.

17. The assembly as in claim 14, wherein the body, lever, and tab are integral and wherein the lever is attached to the body of a living hinge.

18. The assembly as in claim 14, wherein the aperture has a corresponding asymmetric shape relative to the axis.

19. The needle as in claim 14, further comprising a tube movably disposed within the needle, the tube having a proximal end shaped to be engaged by the handle mechanism upon insertion of the body into the handle mechanism.

20. The needle as in claim 14, further comprising a stylet axially movably disposed relative to the hollow of the needle and, wherein the stylet has a key-shaped proximal end which is irrotatably engaged by the handle mechanism upon insertion of the body into the handle mechanism.

* * * * *